(12) United States Patent
Sakurai

(10) Patent No.: US 11,001,547 B2
(45) Date of Patent: May 11, 2021

(54) SYSTEM AND METHOD FOR PRODUCING METHANOL

(71) Applicant: Mitsubishi Heavy Industries Engineering, Ltd., Kanagawa (JP)

(72) Inventor: Mikiya Sakurai, Tokyo (JP)

(73) Assignee: Mitsubishi Heavy Industries Engineering, Ltd., Kanagawa (JP)

( * ) Notice: Subject to any disclaimer, the term of this patent is extended or adjusted under 35 U.S.C. 154(b) by 0 days.

(21) Appl. No.: 15/781,438

(22) PCT Filed: Nov. 11, 2016

(86) PCT No.: PCT/JP2016/083527
§ 371 (c)(1),
(2) Date: Jun. 4, 2018

(87) PCT Pub. No.: WO2017/094475
PCT Pub. Date: Jun. 8, 2017

(65) Prior Publication Data
US 2018/0354877 A1    Dec. 13, 2018

(30) Foreign Application Priority Data
Dec. 4, 2015 (JP) .............................. JP2015-237708

(51) Int. Cl.
*B01J 8/00* (2006.01)
*C07C 29/151* (2006.01)
(Continued)

(52) U.S. Cl.
CPC .............. *C07C 29/151* (2013.01); *C01B 3/24* (2013.01); *C01B 3/36* (2013.01); *C01B 3/386* (2013.01);
(Continued)

(58) Field of Classification Search
None
See application file for complete search history.

(56) References Cited

U.S. PATENT DOCUMENTS 4,927,857 A * 5/1990 McShea, III ............ C01B 3/382
                                                   252/373
5,512,599 A * 4/1996 Hiramatsu .............. C01B 3/382
                                                   518/703
(Continued)

FOREIGN PATENT DOCUMENTS

| CA | 2213025 C | * 6/2006 | ......... C07C 29/1518 |
| EP | 0839786 A2 | 5/1998 | |

(Continued)

OTHER PUBLICATIONS

Pansini et al. Guide to Electric Power Generation, 3rd Edition. 2006. p. 17. (Year: 2006).*

(Continued)

*Primary Examiner* — Jennifer A Leung
(74) *Attorney, Agent, or Firm* — Osha Bergman Watanabe & Burton LLP

(57) ABSTRACT

A method for producing methanol includes obtaining reformed gas by subjecting raw material gas containing methane to partial oxidation reforming by use of oxygen; reducing a $CO/CO_2$ ratio in the reformed gas; and obtaining produced gas containing methanol from the reformed gas with the reduced $CO/CO_2$ ratio by using any of a fixed-bed reactor and an isothermal reactor.

7 Claims, 2 Drawing Sheets

(51) Int. Cl.
*C07C 31/04* (2006.01)
*C01B 3/36* (2006.01)
*C01B 3/48* (2006.01)
*C01B 3/38* (2006.01)
*C07C 29/152* (2006.01)
*C01B 3/24* (2006.01)

(52) U.S. Cl.
CPC ............. *C01B 3/48* (2013.01); *C07C 29/152* (2013.01); *C07C 29/1518* (2013.01); *C07C 31/04* (2013.01); *B01J 2208/00628* (2013.01); *C01B 2203/0255* (2013.01); *C01B 2203/0261* (2013.01); *C01B 2203/0283* (2013.01); *C01B 2203/0405* (2013.01); *C01B 2203/061* (2013.01); *C01B 2203/0883* (2013.01); *C01B 2203/107* (2013.01); *C01B 2203/1064* (2013.01); *C01B 2203/1241* (2013.01); *C01B 2203/148* (2013.01); *C01B 2203/1638* (2013.01)

(56) References Cited

U.S. PATENT DOCUMENTS

| | | | |
|---|---|---|---|
| 6,218,439 B1 | 4/2001 | Kobayashi et al. | |
| 6,255,357 B1 | 7/2001 | Abbott | |
| 6,534,551 B2* | 3/2003 | Allam | C01B 3/38 252/373 |
| 6,706,770 B2* | 3/2004 | Patel | C01B 3/48 518/700 |
| 6,794,418 B2* | 9/2004 | Sogge | C01B 3/36 518/706 |
| 6,846,951 B1* | 1/2005 | Thiebaut | C07C 29/1518 518/700 |
| 7,183,326 B2* | 2/2007 | Davey | C01B 3/025 423/359 |
| 2008/0319093 A1 | 12/2008 | Olah et al. | |
| 2010/0132257 A1 | 6/2010 | Agrawal et al. | |
| 2012/0272567 A1* | 11/2012 | Hawkins | C10K 1/004 44/451 |
| 2015/0141535 A1* | 5/2015 | Kresnyak | C01C 1/04 518/702 |

FOREIGN PATENT DOCUMENTS

| | | | | |
|---|---|---|---|---|
| GB | 2237287 A | * | 5/1991 | ............... C01B 3/36 |
| JP | 2001-97906 A | | 4/2001 | |
| JP | 2002-504111 A | | 2/2002 | |
| JP | 4004550 B2 | | 11/2007 | |
| JP | 2010-132902 A | | 6/2010 | |
| JP | 2010-530878 A | | 9/2010 | |
| RU | 2198838 C1 | | 2/2003 | |

OTHER PUBLICATIONS

Kendall et al. High-temperature Solid Oxide Fuel Cells for the 21st Century: Fundamentals, Design and Applications. 2016. pp. 472-473. (Year: 2016).*
Office Action in corresponding Russian Application No. 2018123184, dated Mar. 11, 2019 (12 pages).
International Preliminary Report on Patentability issued in corresponding International Application No. PCT/JP2016/083527 dated Jun. 5, 2018 (8 pages).
International Search Report issued in corresponding International Application No. PCT/JP2016/083527 dated Dec. 13, 2016 (3 pages).
Notification of Reasons for Refusal in corresponding Japanese Application No. 2015-237708, dated Sep. 13, 2019 (10 pages).

* cited by examiner

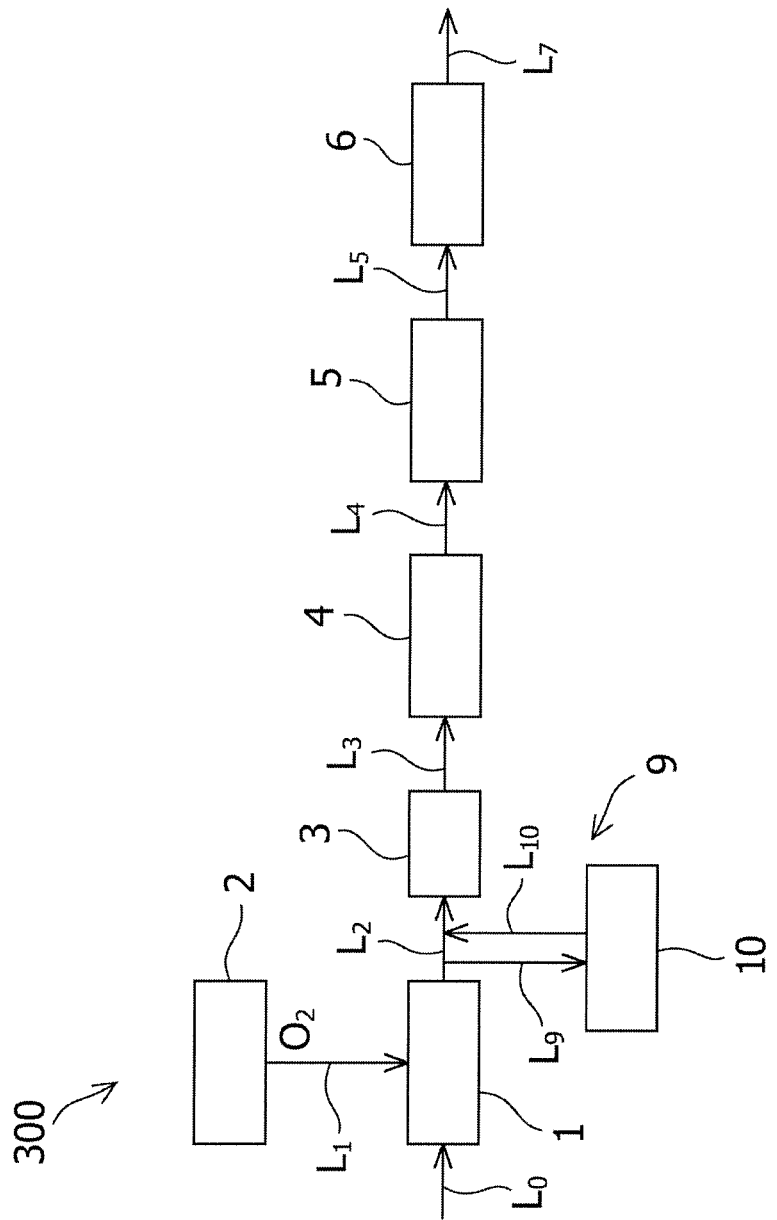

SYSTEM AND METHOD FOR PRODUCING METHANOL

TECHNICAL FIELD

One or more embodiments of the present invention relate to a system and to a method for producing methanol, and to a system and to a method for producing methanol applicable to a system and to a method for co-producing ammonia and methanol.

BACKGROUND

Various methods for producing methanol from natural gas containing methane have heretofore been proposed. In these methods, methanol is synthesized by producing a reformed gas that contains hydrogen, carbon monoxide, and carbon dioxide by reforming methane in natural gas in accordance with steam reforming, autothermal reforming, or the like.

A method designed to perform partial oxidation reforming by introducing oxygen to a gas containing methane in the process of synthesizing methanol has been known as one of the methods for producing methanol (Patent Document 1, for example).

REFERENCE DOCUMENT LIST

Patent Document

Patent Document 1: Japanese Patent No. 4004550

A ratio of an amount of CO relative to an amount of $CO_2$ (a $CO/CO_2$ ratio) is large in the gas modified in accordance with the above-mentioned partial oxidation reforming. As a consequence, an abrupt rise in temperature may occur at the moment of supply of the reformed gas into a methanol production apparatus, thereby imposing a significant burden on the production apparatus. In addition, the rise in temperature accelerates deterioration of the production apparatus as well as structures located inside thereof such as a catalyst. These are reasons it is difficult to apply the partial oxidation reforming to industrial processes.

SUMMARY

In view of the above-mentioned circumstances, one or more embodiments of the present invention provide a system and a method for producing methanol, which may be capable of reducing the burden on an apparatus that produces methanol and the like, and also improving production efficiency of methanol from natural gas.

A method for producing methanol according to one or more embodiments of the present invention is characterized in that the method includes: a reforming step of obtaining a reformed gas by subjecting a raw material gas containing methane to partial oxidation reforming by use of oxygen; a $CO/CO_2$ ratio reducing step of reducing a $CO/CO_2$ ratio in the reformed gas; and a producing step of obtaining a produced gas containing methanol from the reformed gas after the $CO/CO_2$ ratio reducing step.

The $CO/CO_2$ ratio reducing step can adopt a configuration to include introduction of part of the produced gas after the producing step into the reformed gas.

The method for producing methanol can adopt a configuration to further include a pressure boosting step of compressing the reformed gas to boost a pressure of the reformed gas before the producing step, in which the $CO/CO_2$ ratio reducing step includes a $CO_2$ recovering step of recovering $CO_2$ from an exhaust gas from utility equipment in a plant, and the $CO/CO_2$ ratio in the reformed gas is reduced by introducing the $CO_2$ recovered in the $CO/CO_2$ ratio reducing step into the reformed gas before the pressure boosting step.

The method for producing methanol can adopt a configuration to further include a heat recovering step of recovering heat from the reformed gas before the producing step, in which the $CO/CO_2$ ratio reducing step obtains $CO_2$ by bringing part of the reformed gas before the heat recovering step into a shift reaction, and the $CO/CO_2$ ratio is reduced and a temperature of the reformed gas is increased by refluxing the $CO_2$ into the reformed gas before the heat recovering step.

The producing step may involve an isothermal reaction process to synthesize methanol while maintaining uniform temperature in the synthesis.

One or more embodiments of the present invention provide a system for producing methanol. A system for producing methanol according to one or more embodiments of the present invention includes a reforming apparatus configured to obtain a reformed gas by subjecting a raw material gas containing methane to partial oxidation reforming by use of oxygen, a $CO/CO_2$ ratio reduction apparatus configured to reduce a $CO/CO_2$ ratio in the reformed gas, and a production apparatus installed downstream of the $CO/CO_2$ ratio reduction apparatus and configured to obtain a produced gas containing methanol from the reformed gas.

The $CO/CO_2$ ratio reduction apparatus can adopt a configuration to include a line connected from downstream to upstream of the production apparatus and configured to introduce part of the produced gas on the downstream into the reformed gas on the upstream.

The system for producing methanol can adopt a configuration to further include a pressure boosting apparatus configured to compress the reformed gas to boost a pressure of the reformed gas on the upstream of the production processing apparatus, in which the $CO/CO_2$ ratio reduction apparatus includes a $CO_2$ recovery apparatus connected to upstream of the pressure boosting apparatus through a line and configured to recover $CO_2$ from an exhaust gas from utility equipment in a plant, and the $CO/CO_2$ ratio in the reformed gas is reduced by introducing the $CO_2$ from the $CO_2$ recovery apparatus into the reformed gas on the upstream of the pressure boosting apparatus.

The system for producing methanol can adopt a configuration to further include a heat recovery apparatus installed upstream of the production apparatus and configured to recover heat from the reformed gas, in which the $CO/CO_2$ ratio reduction apparatus includes a shift reactor connected to upstream of the heat recovery apparatus through a line, and obtains $CO_2$ by bringing part of the reformed gas on the upstream of the heat recovery apparatus into a shift reaction, and the $CO/CO_2$ ratio is reduced and a temperature of the reformed gas is increased by refluxing the $CO_2$ into the reformed gas on the upstream of the heat recovery apparatus.

The production apparatus may be an isothermal reactor configured to synthesize methanol while maintaining uniform temperature inside the apparatus.

According to one or more embodiments of the present invention, there are provided a system and a method for producing methanol, which may reduce the burden on an apparatus that produces methanol and the like, and also may improve production efficiency of methanol from natural gas.

BRIEF DESCRIPTION OF THE DRAWINGS

FIGS. 1-3 are schematic diagrams showing a system and a method for producing methanol according to various embodiments of the present invention.

DETAILED DESCRIPTION OF THE EMBODIMENTS

A system and a method for producing methanol according to one or more embodiments of the present invention will be described below in detail with reference to the accompanying drawings. The present invention shall not be limited to the embodiments described below. The accompanying drawings are drawings for explaining outlines of one or more embodiments of the system and the method for producing methanol according to the present invention. Hence, devices and instruments attached thereto are partially omitted.

Figure 1:
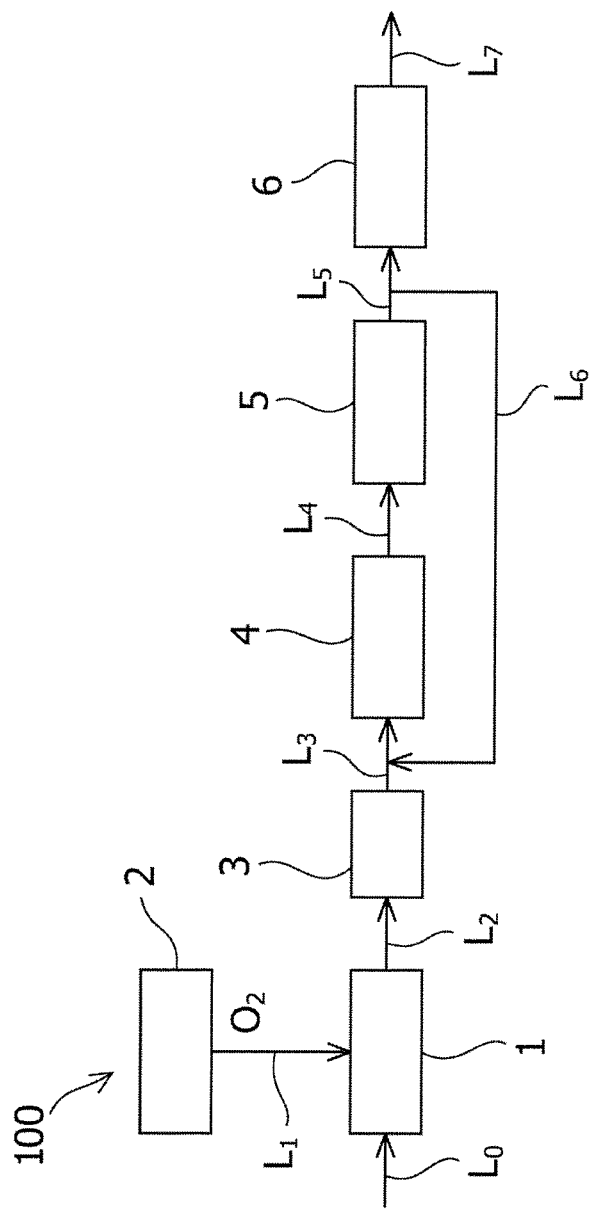

A system for producing methanol according to one or more embodiments of the present invention will be described with reference to FIG. 1. As shown in FIG. 1, a methanol production system 100 of one or more embodiments of the present invention at least includes a reforming apparatus 1, an oxygen plant 2, a heat recovery apparatus 3, a pressure boosting apparatus 4, a production apparatus 5, a $CO/CO_2$ ratio reduction apparatus $L_6$, and a separation apparatus 6.

The reforming apparatus 1 is a partial oxidation reformer configured to obtain a partial oxidation-reformed gas (a reformed gas) that mainly contains carbon monoxide (CO), carbon dioxide ($CO_2$), and hydrogen ($H_2$) from a raw material gas mainly containing methane ($CH_4$) and from oxygen ($O_2$) in accordance with partial oxidation ($PO_x$) reforming. Examples of the partial oxidation reformer include: a direct catalytic partial oxidizer with a reforming catalyst placed inside for reforming a raw material gas; a non-catalytic partial oxidizer with no reforming catalyst placed inside; and the like. Examples of the reforming catalyst include noble metal catalysts such as platinum (Pt) and rhodium (Rh). In addition, the raw material is natural gas. The raw material gas only needs to be a raw material that contains methane. In this regard, coal gas, coke gas, and the like can also be used in addition to the natural gas. The reforming apparatus 1 is connected to a raw material gas supply line $L_0$ for introducing the raw material gas to the inside, a line $L_1$ for introducing oxygen from the oxygen plant 2, and a line $L_2$ for introducing the reformed gas into the heat recovery apparatus 3, respectively.

The oxygen plant 2 is a facility which is installed in a plant and configured to separate oxygen by cooling the air in accordance with cryogenic separation. The oxygen plant 2 is connected to the line $L_1$ for supplying the separated oxygen to the reforming apparatus 1. Alternatively, the oxygen plant 2 may be a facility located outside the plant. For example, an oxygen plant installed in a different methanol plant or in another chemical plant or the like is applicable. When the oxygen plant is shared with a different plant, it is possible to improve production efficiency required for co-production of methanol or of methanol and other substances in multiple plants.

The heat recovery apparatus 3 is a heat exchanger which is installed downstream of the reforming apparatus 1 and configured to exchange heat between the reformed gas and a medium (such as water) and thus to recover heat from the reformed gas in the form of steam. The heat recovery apparatus 3 is connected to a line $L_3$ for introducing the reformed gas deprived of the heat into the pressure boosting apparatus 4. This line $L_3$ is connected to the $CO/CO_2$ ratio reduction apparatus $L_6$ for introducing a gas at a low $CO/CO_2$ ratio, to be described later, into the reformed gas.

The pressure boosting apparatus 4 is a compressor installed downstream of the heat recovery apparatus 3. The compressor only needs to be an apparatus which can boost the pressure of a produced gas. For example, a centrifugal compressor that applies the high pressure gas generated by the heat recovery apparatus to a power source can be employed as the compressor. The pressure boosting apparatus 4 is connected to a line $L_4$ for introducing the boosted reformed gas into the production apparatus 5.

The production apparatus 5 is an isothermal reactor which is installed downstream of the pressure boosting apparatus 4 and configured to obtain the produced gas containing methanol ($CH_3OH$) from the reformed gas containing any of CO and $CO_2$ as well as hydrogen. The production apparatus 5 only needs to be an apparatus which can synthesize methanol from the reformed gas. To be more precise, examples of the production apparatus 5 include: fixed-bed, fluidized-bed, and entrained-bed reactors; a microchannel reactor; the isothermal reactor; and the like. Among them, the production apparatus 5 may be any of the fluidized-bed reactor, the entrained-bed reactor, the microchannel reactor, and the isothermal reactor, or the isothermal reactor. Each of these apparatuses can make the heat uniform by controlling the occurrence of locally high temperatures inside the apparatus, and reduce a burden on the production apparatus itself as well as instruments and/or a methanol synthesis catalyst inside the apparatus. The methanol synthesis catalyst such as a copper-based catalyst for synthesizing methanol from the reformed gas is disposed inside the production apparatus 5. The production apparatus 5 is connected to a line $L_5$ for introducing part of the produced gas containing methanol into the separation apparatus 6. This line $L_5$ is connected to the $CO/CO_2$ ratio reduction apparatus $L_6$ for refluxing the remaining part of the produced gas at the low $CO/CO_2$ ratio.

The above-described isothermal reactor may be more preferably an SPC (super converter). The SPC is a type of isothermal reactor which pre-heats a feed gas with reaction heat and to generate steam with the reaction heat. In this way, it is possible to render the temperature of a catalyst layer more uniform at the time of the reaction.

The $CO/CO_2$ ratio reduction apparatus $L_6$ is a line for controlling the $CO/CO_2$ ratio of the reformed gas on the upstream of the production apparatus 5. One end of the $CO/CO_2$ ratio reduction apparatus $L_6$ is connected to the line $L_5$ and the other end thereof is connected to the line $L_3$. The $CO/CO_2$ ratio reduction apparatus $L_6$ is configured to reduce the $CO/CO_2$ ratio of the reformed gas by refluxing the produced gas at the low $CO/CO_2$ ratio on the downstream of the production apparatus 5 to the downstream of the heat recovery apparatus 3 (in other words, the upstream of the pressure boosting apparatus 4). The $CO/CO_2$ ratio corresponds to the amount (a mole ratio) of CO relative to the amount of $CO_2$ in the reformed gas or the produced gas.

The separation apparatus 6 is a distillation column, for instance, which separates the produced gas containing methanol into methanol and by-products. The by-products are classified roughly into low boiling-point and high boiling-point compounds. The separation apparatus 6 is connected to a line $L_7$ for supplying the separated and refined methanol as a product or as a raw material in another plant, and to a discharge line (not shown) for discharging the by-products.

Next, the method of a system for producing methanol according to one or more embodiments of the present invention will be described below in detail by explaining a mode of operation of the methanol production system 100 having the above-mentioned configuration. The method for producing methanol of one or more embodiments of the present invention includes a reforming step, a heat recovering step, a CO/CO$_2$ ratio reducing step, a pressure boosting step, a producing step, and a refining step.

In the reforming step, the raw material gas, which mainly contains methane, and oxygen from the oxygen plant 2 are introduced into the reforming apparatus 1. In the reforming step, reactions to produce the reformed gas containing CO, CO$_2$, and hydrogen from methane and oxygen as expressed in the following formulae (1) to (3) proceed dominantly in accordance with the partial oxidation reforming:

[Chemical 1]

$$CH_4 + \tfrac{1}{2}O_2 \rightarrow 2H_2 + CO \tag{1}$$

$$CO + \tfrac{1}{2}O_2 \rightarrow CO_2 \tag{2}$$

$$H_2 + \tfrac{1}{2}O_2 \rightarrow H_2O \tag{3}$$

In addition, the partial oxidation reforming in the reforming step represents a reaction to introduce oxygen to a reaction system and to supply the heat required for the reforming by oxidizing part of the raw material gas. Examples of the above-mentioned partial oxidation reforming include non-catalytic partial oxidation (non-catalytic PO$_x$) which uses the aforementioned non-catalytic partial oxidizer, direct catalytic partial oxidation (D-CPOX) which uses the direct catalytic partial oxidizer, and the like. In the case of using the non-catalytic partial oxidation, a reaction temperature can be set in a range from 1200° C. to 1550° C. and a reaction pressure can be set in a range from 3.0 to 7.0 MPa, for example. Meanwhile, in the case of using the direct catalytic partial oxidation, a reaction temperature can be set in a range from 700° C. to 900° C. and a reaction pressure can be set in a range from 1.0 to 2.0 MPa, for example.

Subsequently, in the heat recovering step, the reformed gas after the reforming step is introduced into the heat recovery apparatus 3, and the heat exchange between the reformed gas heated to a high temperature as a consequence of heat generation in the reforming reaction and the water medium is conducted to recover the heat from the reformed gas in the form of steam. Meanwhile, as described later, the gas with the reduced CO/CO$_2$ ratio after undergoing the CO/CO$_2$ ratio reducing step is introduced into the reformed gas after the heat recovery.

Next, in the pressure boosting step, the produced gas after the heat recovering step is introduced into the pressure boosting apparatus 4, and the pressure of the produced gas is boosted by compression to a predetermined range suitable for the synthesis of methanol such as a range from 5.0 to 15 MPa.

Subsequently, in the producing step, methanol is synthesized by reactions expressed in the following formulae (4) and (5) from CO, CO$_2$, and hydrogen in the produced gas after the pressure boosting step, thereby obtaining the produced gas at least containing methanol:

[Chemical 2]

$$CO_2 + 2H_2 \leftrightarrow CH_3OH \tag{4}$$

$$CO_2 + 3H_2 \leftrightarrow CH_3OH + H_2O \tag{5}$$

In the producing step, a local rise in temperature in the apparatus is prevented by using the production apparatus 5, which is the isothermal reactor, thus making uniform and controlling the temperature within a preferable range. Accordingly, it is possible to reduce the burden on the apparatus as well as the instruments and/or the catalyst in the inside caused by the heat of the synthesis reaction. The reaction temperature required for the synthesis of methanol falls in a range from 100° C. to 300° C. and may be set in a range from 150° C. to 250° C. Meanwhile, the produced gas at a controlled CO/CO$_2$ ratio is obtained in this step by increasing the CO/CO$_2$ ratio until a sufficient additive ratio of methanol is achieved in the reforming step while applying the partial oxidation reforming, and then controlling the CO/CO$_2$ ratio by conducting the CO/CO$_2$ ratio reducing step. Thus, it is possible to reduce the number of times of methanol synthesis reactions, i.e., the number of times of the producing step, and to further reduce the burden on the production apparatus as well as the instruments and/or the catalyst thereof caused by the heat of the synthesis reaction.

In the CO/CO$_2$ ratio reducing step, part of the produced gas after the producing step is separated and recovered by the CO/CO$_2$ ratio reduction apparatus L$_6$, and is introduced and refluxed into the reformed gas after the heat recovering step (before the pressure boosting step). The CO/CO$_2$ ratio in the produced gas after the producing step is lower than the CO/CO$_2$ ratio in the reformed gas after the heat recovering step. Accordingly, in this step, the CO/CO$_2$ ratio in the reformed gas before the producing step is reduced so as to control the ratio within a predetermined range.

According to one or more embodiments, the CO/CO$_2$ ratio in the gas controlled in the CO/CO$_2$ ratio reducing step falls into a range from not less than 0.5 and not more than 5.0, or preferably in a range from not less than 1.2 and not more than 4.0 or more preferably in a range from not less than 1.4 and not more than 3.5. In this range, it is possible to achieve a high conversion ratio of methanol in the producing step, and also to reduce the burden on the production apparatus as well as the instruments and/or the catalyst in the inside caused by the heat generated in the methanol synthesis reaction.

Subsequently, in a refining step, the methanol-containing produced gas after the producing step and/or the CO/CO$_2$ ratio reducing step is introduced into the separation apparatus 6 through the line L$_5$, and is separated into highly pure methanol and the low boiling-point and high boiling-point compounds constituting the by-products in accordance with distilled separation. The highly pure methanol is recovered through the line L$_7$ while the by-products are discharged from the system as wastewater. The methanol thus separated may be released as a product or used as a production raw material in an ammonia plant, an acetic acid plant, and the like annexed to this plant. By using the methanol thus produced as the raw material for ammonia, acetic acid, and the like, the methanol production efficiency of this embodiment can also be shared with the production of ammonia, acetic acid, and the like.

The production of methanol from the raw material gas is carried out as described above. According to this embodiment, it is possible to prevent development of the methanol synthesis reaction, which is an exothermal reaction, at the moment of supply of the reformed gas into the production apparatus 5 by controlling the CO/CO$_2$ ratio in the reformed gas produced in accordance with the partial oxidation reforming. As a consequence, it is possible to prevent a thermal burden on the production apparatus itself as well as the instruments in the apparatus and/or the catalyst inside the apparatus due to a significant rise in temperature. In addition, sufficient reaction activity can be obtained thanks to the reforming step that applies the partial oxidation reforming.

Accordingly, it is possible to improve the production efficiency of methanol by reducing the number of times of the producing step to meet the required amount of methanol.

Figure 2:
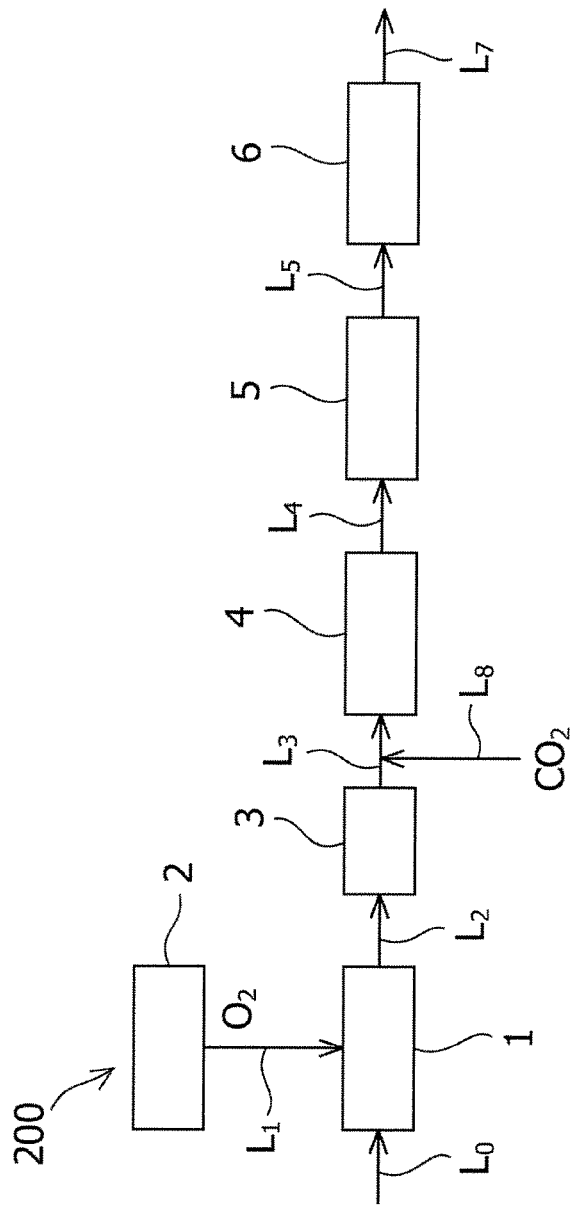

A system and the method for producing methanol according to one or more embodiments of the present invention will be described below in detail with reference to FIG. 2. The same constituents as those described above will be denoted by the same reference symbols and explanations thereof will be omitted. As shown in FIG. 2, a methanol production system 200 of this embodiment is different from the production system 100 mainly in that a $CO/CO_2$ ratio reduction apparatus $L_8$ is provided instead of the above-described $CO/CO_2$ ratio reduction apparatus $L_6$.

The $CO/CO_2$ ratio reduction apparatus $L_8$ is a line configured to control the $CO/CO_2$ ratio of the reformed gas on the downstream of the pressure boosting apparatus 4. One end of the $CO/CO_2$ ratio reduction apparatus $L_8$ is connected to the line $L_3$ and the other end thereof is connected to a $CO_2$ recovery apparatus (not shown). The $CO_2$ recovery apparatus is configured to recover $CO_2$ from an exhaust gas from utility equipment in this plant. Thus, it is possible to reduce the $CO/CO_2$ ratio in the reformed gas on the line $L_3$ between the heat recovery apparatus 3 and the temperature raising apparatus 4, and to improve the production efficiency by efficiently using $CO_2$ in the exhaust gas produced by the utility equipment while contributing to reduction of $CO_2$ emission at the same time. The utility equipment is not limited to particular equipment as long as the equipment emits a $CO_2$-containing gas. Example of the utility equipment include an auxiliary boiler installed at a steam system, a GTG (gas turbine generator) for supplying electric power, a fired heater for starting up the plant, and the like. The utility equipment is not limited to the equipment installed at the original plant. For example, as the utility equipment, it is possible to share other utility equipment installed at a different methanol plant, an ammonia plant, or the like annexed to the original plant. In addition, a steam reformer installed in the inside or outside of the plant and configured to emit a $CO_2$-containing gas may be employed instead of the utility equipment. Thus, it is possible to make efficient use of $CO_2$ required for the co-production of methanol, ammonia, and the like while involving the different plant, to improve the production efficiency thereof, and to contribute to the reduction in $CO_2$ emission.

The $CO_2$ recovery apparatus is not limited to a particular apparatus as long as the apparatus can recover $CO_2$ from the exhaust gas. More exactly, the $CO_2$ recovery apparatus may be a $CO_2$ separation column including any of an amine absorption liquid that absorbs $CO_2$, and an inorganic separation membrane made of zeolite of DDR-type, CHA-type, and the like. The $CO_2$ recovery apparatus is not limited to the equipment or the apparatus installed in the original plant. For example, it is possible to share another $CO_2$ recovery apparatus which is installed at a different methanol plant, an ammonia plant, or the like annexed to the original plant. Thus, it is possible to improve the production efficiency of methanol, ammonia, and the like while involving the different plant.

In addition, the main difference between the method for producing methanol of this embodiment and that of the first embodiment lies in the $CO/CO_2$ ratio reducing step mentioned above. In the $CO/CO_2$ ratio reducing step, $CO_2$ recovered in the $CO_2$ recovering step from the exhaust gas from the utility equipment inside the plant is introduced into the reformed gas after the heat recovering step and before the pressure boosting step, thereby reducing the $CO/CO_2$ ratio in the reformed gas. In the $CO_2$ recovering step, $CO_2$ is recovered from the exhaust gas generated in the utility equipment and a $CO_2$-rich gas mainly containing $CO_2$ is produced therefrom. Examples of a method applicable in the $CO_2$ recovering step include chemical absorption, membrane separation, and the like. In the chemical absorption, $CO_2$ in the exhaust gas is absorbed by the amine absorption liquid, and then the liquid is heated to separate and recover $CO_2$ therefrom. Meanwhile, in the membrane separation, the exhaust gas is transported across the inorganic separation membrane so as to selectively separate and recover $CO_2$. The $CO_2$ recovering step makes it possible to obtain the $CO_2$-rich gas at a low $CO/CO_2$ ratio, i.e., with $CO_2$ at a high purity, and thus, to facilitate the control of the $CO/CO_2$ ratio in the reformed gas.

A system and the method for producing methanol according to one or more embodiments of the present invention will be described below in detail with reference to FIG. 3. The same constituents as those described above in FIGS. 1 and 2 will be denoted by the same reference symbols and explanations thereof will be omitted. As shown in FIG. 3, a methanol production system 300 of this embodiment is different from the production system 100 mainly in that a $CO/CO_2$ ratio reduction apparatus 9 is provided instead of the above-described $CO/CO_2$ ratio reduction apparatus $L_6$.

The $CO/CO_2$ ratio reduction apparatus 9 is provided with a shift reactor 10 and configured to convert part of the reformed gas into the $CO_2$-rich gas by a shift reaction and to reflux the $CO_2$-rich gas on the downstream of the reforming apparatus 1 and the upstream of the heat recovery apparatus 3. In this way, the $CO/CO_2$ ratio in the reformed gas is reduced. The $CO/CO_2$ ratio reduction apparatus 9 includes a line $L_9$ for introducing the reformed gas on the line $L_2$ into the shift reactor 10 and a line $L_{10}$ for refluxing the gas produced by the shift reactor 10 onto the line $L_2$.

In addition, the method for producing methanol as described in FIG. 3 is different from the one described in FIG. 1 mainly in the above-described $CO/CO_2$ ratio reducing step. In the $CO/CO_2$ ratio reducing step, the reformed gas after the reforming step is introduced into the $CO/CO_2$ ratio reduction apparatus 9, and hydrogen is produced from the steam ($H_2O$), CO, and $CO_2$ by the shift reaction in the shift reactor 10 as expressed in the following formula (6). In the meantime, since the $CO_2$-rich gas reaches a high temperature by the heat generation in the shift reaction, this step can reduce the $CO/CO_2$ ratio after the reforming step and increase the amount of heat to be recovered in the heat recovering step. A reaction temperature required for the shift reaction falls in a range from 200° C. to 400° C., and a reaction pressure can be set in a range from 2.0 to 4.0 MPa, for example:

[Chemical 3]

$$H_2O+CO \rightarrow H_2+CO_2 \qquad (6)$$

The steam used in the shift reaction process is produced by a side reaction in the reforming step and is contained in the reformed gas. If the steam is insufficient, it is possible to introduce steam, which is in excess, in the heat recovery apparatus 3, the pressure boosting apparatus 4, and/or a device outside the original plant. Examples of the device outside the original plant include an auxiliary boiler installed in the ammonia plant annexed to the original plant, and the like. In this way, the steam outside the original plant can be effectively used in the system. Meanwhile, hydrogen produced in the shift reaction process can be introduced into the reformed gas after the heat recovering step and used for the synthesis of methanol in the producing step. If hydrogen becomes excessive in the producing step, then such hydrogen can be separated from the reformed gas by providing separation membrane (not shown), and this hydrogen can be refluxed into the reforming apparatus 1 for use in the reforming step, for example. Thus, it is possible to reduce the amount of oxygen to be supplied from the oxygen plant 2 and to make efficient use of hydrogen on the inside and outside of the original plant in the production of methanol.

In the above-mentioned embodiments, the $CO/CO_2$ ratio reduction apparatuses and the $CO/CO_2$ ratio reducing steps have been described as alternatives, respectively. However, one or more embodiments of the present invention are not limited to this configuration. For example, two out of the $CO/CO_2$ ratio reduction apparatus $L_6$, the $CO/CO_2$ ratio reduction apparatus $L_8$, and the $CO/CO_2$ ratio reduction apparatus 9 may be installed and the $CO/CO_2$ ratio reducing step may be conducted by using these apparatuses. Otherwise, all the $CO/CO_2$ ratio reduction apparatuses $L_6$, $L_8$, and 9 may be installed and the $CO/CO_2$ ratio reducing step may be conducted by using all of the apparatuses.

EXAMPLES

Effects of one or more embodiments of the present invention will be clarified by explaining examples of the present invention. The system and the method for producing methanol according to one or more embodiments of the present invention are not limited to these examples.

Test Example 1

A maximum value of the temperature locally occurring in the reactor during the synthesis of methanol was measured in a plant configured to use a non-catalytic partial oxidizer as the reforming apparatus and a fixed-bed reactor as the reaction apparatus, and not provided with the methanol plant of the first embodiment except the $CO/CO_2$ ratio reduction apparatus. The reaction temperature inside the reforming apparatus was set to 1300° C. and the reaction pressure inside the reforming apparatus was set to 4.0 MPa. The reaction temperature inside the reaction apparatus was set to 250° C. and the reaction pressure inside the reaction apparatus was set to 10 MPa.

Test Example 2

A maximum value of the temperature locally occurring in the reactor during the synthesis of methanol was measured in a plant configured to use the non-catalytic partial oxidizer as the reforming apparatus and the fixed-bed reactor as the reaction apparatus, and provided with the methanol plant of the first embodiment including the $CO/CO_2$ ratio reduction apparatus. The reaction temperature and the reaction pressure inside the reforming apparatus were set equal to the values in test example 1, while the reaction temperature inside the reaction apparatus was set to 250° C. and the reaction pressure inside the reaction apparatus was set to 10 MPa. The $CO/CO_2$ ratio of the reformed gas on the upstream of the reaction apparatus was set to 4.0 by using the $CO/CO_2$ ratio reduction apparatus.

Test Example 3

A maximum value of the temperature locally occurring in the reactor during the synthesis of methanol was measured in a plant configured to use the non-catalytic partial oxidizer as the reforming apparatus and the SPC as the reaction apparatus, and provided with the methanol plant of the first embodiment including the $CO/CO_2$ ratio reduction apparatus. The reaction temperature and the reaction pressure inside the reforming apparatus were set equal to the values in test example 1, while the reaction temperature inside the reaction apparatus was set to 250° C. and the reaction pressure inside the reaction apparatus was set to 10 MPa. The $CO/CO_2$ ratio of the reformed gas upstream of the reaction apparatus was set to 4.0 by using the $CO/CO_2$ ratio reduction apparatus.

The maximum value of the local temperature occurring in the synthesis of methanol with the reaction apparatus of test example 1 was 500° C. The maximum value of the local temperature occurring in the synthesis of methanol with the reaction apparatus of test example 2 was 350° C. The maximum value of the local temperature occurring in the synthesis of methanol with the reaction apparatus of test example 3 was 270° C.

From the results, it was confirmed that the local temperature occurring inside the reactor could be lowered so that the burden on the production apparatus could be reduced more than test example 1 when carrying out the $CO/CO_2$ ratio reducing step by providing the $CO/CO_2$ ratio reduction apparatus (test example 2). In addition, it was confirmed that the local temperature occurring inside the reactor could be lowered so that the burden on the production apparatus could be reduced more than test example 2 when carrying out the $CO/CO_2$ ratio reducing step while replacing the production apparatus in test example 2 with the SPC (test example 3).

According to the system and the method for producing methanol of one or more embodiments of the present invention, it is possible to reduce a burden on an apparatus that produces methanol and to improve production efficiency of methanol from natural gas.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

REFERENCE SYMBOL LIST 1 reforming apparatus
2 oxygen plant
3 heat recovery apparatus
4 pressure boosting apparatus
5 production apparatus
6 separation apparatus
$L_6$, $L_8$, 9 $CO/CO_2$ ratio reduction apparatus
10 shift reactor
100, 200, 300 methanol production system

The invention claimed is:

1. A system for producing methanol, comprising in order, from upstream to downstream:
   a non-catalytic partial oxidation reforming apparatus that obtains reformed gas by subjecting raw material gas containing methane to non-catalytic partial oxidation reforming by use of oxygen;
   a single heat recovery apparatus that is directly downstream from the reforming apparatus that recovers heat from the reformed gas;
   a pressure boosting apparatus that is directly downstream from the single heat recovery apparatus that compresses the reformed gas;

a production apparatus that obtains produced gas containing methanol from the reformed gas by using any of a fixed-bed reactor and an isothermal reactor; and a separation apparatus that separates the produced gas containing methanol into methanol and by-products;

wherein the system further comprises a first, a second, and a third $CO/CO_2$ ratio reduction apparatus, each of which has first and second ends and reduces a $CO/CO_2$ ratio in the reformed gas;

wherein, in the first CO/CO2 ratio reduction apparatus, only the first end is connected between the single heat recovery apparatus and the pressure boosting apparatus, wherein the first $CO/CO_2$ ratio reduction apparatus is connected from downstream to upstream of the production apparatus and introduces part of the produced gas on the downstream into the reformed gas on the upstream;

wherein, in the second CO/CO2 ratio reduction apparatus, the first and second ends are connected between the reforming apparatus and the single heat recovery apparatus;

wherein the third $CO/CO_2$ ratio reduction apparatus includes a $CO_2$ recovery apparatus connected upstream of the pressure boosting apparatus through a line that has the first and second ends and that recovers $CO_2$ from exhaust gas from utility equipment in a plant, and the $CO/CO_2$ ratio in the reformed gas is reduced by introducing the recovered $CO_2$ from the $CO_2$ recovery apparatus into the reformed gas upstream of the pressure boosting apparatus; and wherein the non-catalytic partial oxidation reforming apparatus contains no reforming catalyst.

2. The system for producing methanol according to claim 1, wherein the production apparatus is an isothermal reactor that synthesizes methanol while making a temperature inside the apparatus uniform.

3. The system for producing methanol according to claim 2, wherein the isothermal reactor is a super converter that pre-heats the reformed gas with reaction heat and generates steam with the reaction heat.

4. The system for producing methanol according to claim 1,
wherein the first end of the line of the third $CO/CO_2$ ratio reduction apparatus is connected between the single heat recovery apparatus and the pressure boosting apparatus, and the second end is connected between the production apparatus and the separation apparatus.

5. The system for producing methanol according to claim 1, wherein the first end of the line of the third $CO/CO_2$ ratio reduction apparatus is connected between the heat recovery apparatus and the pressure boosting apparatus, and the second end is connected to the $CO_2$ recovery apparatus.

6. The system for producing methanol according to claim 1, wherein the first, the second, and the third $CO/CO_2$ ratio reduction apparatuses control the $CO/CO_2$ ratio in the reformed gas to be 0.5 to 5.0.

7. The system for producing methanol according to claim 1, wherein the non-catalytic partial oxidation comprises the following chemical reactions, which supply the heat required for the reforming:
the oxidation of methane to give hydrogen and carbon monoxide;
the oxidation of carbon monoxide to give carbon dioxide; and
the oxidation of hydrogen to give water.

* * * * *